United States Patent
Plocher et al.

(10) Patent No.: US 12,343,494 B1
(45) Date of Patent: Jul. 1, 2025

(54) ADAPTABLE CONNECTOR FOR UROSTOMY BAGS

(71) Applicant: GV SOLUTIONS LLC, Camp Hill, PA (US)

(72) Inventors: Jacob Karl Plocher, Lancaster, PA (US); Marion R. Green, Camp Hill, PA (US)

(73) Assignee: GV Solutions LLC, Camp Hill, PA (US)

( * ) Notice: Subject to any disclaimer, the term of this patent is extended or adjusted under 35 U.S.C. 154(b) by 0 days.

(21) Appl. No.: 19/186,145

(22) Filed: Apr. 22, 2025

Related U.S. Application Data

(63) Continuation of application No. 18/981,067, filed on Dec. 13, 2024, now Pat. No. 12,290,657.

(60) Provisional application No. 63/610,128, filed on Dec. 14, 2023.

(51) Int. Cl.
   *A61M 39/12* (2006.01)
   *A61F 5/44* (2006.01)
   *A61F 5/445* (2006.01)
   *A61M 39/10* (2006.01)

(52) U.S. Cl.
   CPC ........... *A61M 39/12* (2013.01); *A61F 5/4405* (2013.01); *A61F 5/445* (2013.01); *A61M 2039/1077* (2013.01)

(58) Field of Classification Search
   CPC ........... A61M 39/12; A61M 2039/1077; A61F 5/4405; A61F 5/445
   See application file for complete search history.

(56) References Cited

U.S. PATENT DOCUMENTS

| | | | | |
|---|---|---|---|---|
| 3,415,299 A | * | 12/1968 | Hinman, Jr. | A61F 5/44 604/326 |
| 3,823,716 A | * | 7/1974 | Hale | A61F 5/44 604/335 |
| 4,084,590 A | * | 4/1978 | Caraway | A61F 5/445 604/350 |
| 4,238,059 A | * | 12/1980 | Caraway | A61F 5/4405 285/332 |

(Continued)

FOREIGN PATENT DOCUMENTS

| | | |
|---|---|---|
| AU | 6343680 A | 4/1981 |
| CA | 1160126 A | 1/1984 |

(Continued)

*Primary Examiner* — Guy K Townsend
(74) *Attorney, Agent, or Firm* — Saxton & Stump, LLC

(57) ABSTRACT

A method for assembling an ostomy bag and drain assembly, a drain assembly, and an adaptable connector to provide both greater discreet drainage of the urine waste from an ostomy bag and greater control of the flow of the urine waste. The method includes providing a connector having a barrel body, directing the connector into engagement with a mating feature of the ostomy bag, directing a flexible conduit over an end of the connector to connect and seal the flexible conduit to the connector, and directing a distal end of the flexible conduit onto a discharge valve to attach and seal the flexible conduit to the connector. The barrel body engages the mating feature to establish a leak-free interface with the first portion or the second portion corresponding to a diameter of the mating feature. A drain assembly and adaptable connector are also disclosed.

20 Claims, 6 Drawing Sheets

(56) References Cited

U.S. PATENT DOCUMENTS

| | | | |
|---|---|---|---|
| 4,254,771 A * | 3/1981 | Vidal | A61F 5/441 604/325 |
| 4,280,498 A * | 7/1981 | Jensen | A61F 5/4405 604/323 |
| 4,300,560 A | 11/1981 | Steer | |
| 4,540,156 A * | 9/1985 | Cross | F16K 31/602 604/350 |
| 4,573,983 A * | 3/1986 | Annis | A61F 5/441 600/580 |
| 4,592,750 A | 6/1986 | Kay | |
| 4,634,437 A * | 1/1987 | Lowthian | A61F 5/44 600/580 |
| D300,361 S * | 3/1989 | Tokarz | D24/129 |
| 4,889,533 A | 12/1989 | Beecher | |
| 4,909,478 A * | 3/1990 | Steer | F16K 5/0414 604/323 |
| 5,098,420 A | 3/1992 | Iacone | |
| 5,299,777 A * | 4/1994 | Milstead | F01M 11/0408 251/291 |
| 6,132,408 A * | 10/2000 | Lutz | A61F 5/4407 604/335 |
| 6,224,581 B1 | 5/2001 | Withers | |
| 6,726,667 B2 | 4/2004 | Leise, Jr. et al. | |
| 7,008,407 B1 * | 3/2006 | Kamp | A61F 5/4405 604/327 |
| 7,223,260 B2 | 5/2007 | Hansen et al. | |
| 7,476,220 B2 | 1/2009 | Lillegard | |
| 7,879,015 B2 | 2/2011 | Villefrance et al. | |
| D649,241 S | 11/2011 | Kunishige | |
| 8,292,858 B2 * | 10/2012 | Burgess | A61F 5/4405 604/326 |
| 8,882,732 B2 * | 11/2014 | March | A61F 5/445 604/332 |
| 9,333,110 B2 * | 5/2016 | March | A61F 5/445 |
| 10,251,770 B2 * | 4/2019 | Chang | A61F 5/445 |
| D910,170 S | 2/2021 | Scalise et al. | |
| 11,000,400 B2 | 5/2021 | Grum-Schwensen et al. | |
| 11,065,144 B2 | 7/2021 | Nielsen et al. | |
| D978,345 S * | 2/2023 | Green | D24/129 |
| 11,701,249 B2 * | 7/2023 | Green | A61F 5/445 604/335 |
| 11,951,028 B2 * | 4/2024 | Green | A61F 5/4405 |
| 12,290,657 B1 * | 5/2025 | Plocher | A61M 39/12 |
| 2005/0273065 A1 | 12/2005 | Lillegaard | |
| 2006/0155252 A1 | 7/2006 | Walker et al. | |
| 2009/0163883 A1 | 6/2009 | Christensen | |
| 2010/0298789 A1 | 11/2010 | Santimaw | |
| 2012/0130329 A1 * | 5/2012 | March | F16K 3/24 604/332 |
| 2013/0338616 A1 * | 12/2013 | Galindo | A61F 5/4405 604/335 |
| 2015/0025483 A1 * | 1/2015 | March | A61F 5/4405 604/318 |
| 2015/0190272 A1 * | 7/2015 | Chang | A61F 5/445 604/335 |
| 2019/0231582 A1 * | 8/2019 | Købke | A61F 5/451 |
| 2020/0046543 A1 | 2/2020 | Scalise et al. | |
| 2021/0022911 A1 * | 1/2021 | Scalise | A61F 5/4407 |
| 2021/0251795 A1 * | 8/2021 | Holroyd | A61F 5/4405 |
| 2021/0251796 A1 * | 8/2021 | Holroyd | A61F 5/4405 |
| 2021/0251797 A1 | 8/2021 | Holroyd | |
| 2021/0259874 A1 | 8/2021 | Oellgaard | |
| 2022/0142808 A1 | 5/2022 | Weinberg et al. | |
| 2023/0138034 A1 * | 5/2023 | Green | A61F 5/4404 604/335 |
| 2023/0270581 A1 * | 8/2023 | Green | A61F 5/445 604/323 |
| 2024/0245542 A1 * | 7/2024 | Green | A61F 5/445 |

FOREIGN PATENT DOCUMENTS

| | | |
|---|---|---|
| CA | 3049266 A | 7/2018 |
| CN | 1265772 C | 7/2006 |
| CN | 1311791 C | 4/2007 |
| CN | 106535836 B | 12/2018 |
| EP | 1221916 B1 | 8/2004 |
| EP | 2642956 B1 | 7/2017 |
| GB | 2593013 A | 9/2021 |
| JP | 5261363 B2 | 5/2013 |
| WO | 2016008495 A1 | 1/2016 |
| WO | 2019221830 A1 | 11/2019 |
| WO | 2021165675 A1 | 8/2021 |
| WO | 2021165676 A1 | 8/2021 |

* cited by examiner

ADAPTABLE CONNECTOR FOR UROSTOMY BAGS

RELATED APPLICATIONS

This application is a continuation of and claims priority to U.S. patent application Ser. No. 18/981,067, filed Dec. 13, 2024, entitled, "ADAPTABLE CONNECTOR FOR UROSTOMY BAGS", which claims priority to U.S. Provisional Patent Application 63/610,128, filed Dec. 14, 2023, entitled, "UNIVERSAL CONNECTOR FOR UROSTOMY POUCHES", each of which is incorporated by reference herein in its entirety.

FIELD OF THE INVENTION

The present disclosure is generally directed to an apparatus and method for connecting of various products to urostomy or ostomy bags or pouches to allow drainage of bodily fluids, such as urine, in various ways.

BACKGROUND OF THE INVENTION

The various manufacturers of ostomy or urostomy bags, used to store bodily fluids drained from the body by way of a stoma, have designed connectors, unique to each manufactured bag, used to connect various products to the drain of the urostomy bag. These include connecting tubes leading to over-night drain bags, and connectors which can be used to connect the BobTail™ drain. Some bags have a long pin like device to pinch the bottom of the bag closed. Others have valves that either are openings which can be plugged or a valve that turns open or closed.

The unique connectors and unique ostomy bag interfaces make it cumbersome and difficult to adapt various products to the bag for some products are designed for a particular manufactured bag.

The invention includes the design of a single connector that will connect to almost all urostomy bags making it easier and more convenient to connect a large variety of products to essentially any bag.

What is needed is an apparatus and method for connecting various products to urostomy or ostomy bags or pouches that does not suffer from the drawbacks of the prior art. Other features and advantages will be made apparent from the present specification. The teachings disclosed extend to those embodiments that fall within the scope of the claims, regardless of whether they accomplish one or more of the aforementioned needs.

SUMMARY OF THE INVENTION

The present disclosure is directed to a drain assembly and urostomy bag arrangement that allows user to discreetly and more accurately empty bags of waste. The drain assembly arrangement according to the present disclosure allows users to use the device while at a toilet by simply moving the flexible conduit with the discharge valve to direct its discharge to the toilet and opening the valve. The drain assembly allows users to easily sit or stand while draining the urostomy bag into the toilet. It affords privacy and accuracy for all users. An adaptable connector according to the present disclosure allows the drain assembly to be connected to a variety of urostomy bags or pouches having differing discharge configurations while providing a secure and leak-free connection.

In an embodiment, an adaptable connector includes a barrel body with a first end, a first portion adjacent to the first end, a second portion, and a transition portion disposed between the first and second portions. The first portion has a circumferential surface having a first diameter. The second portion has a circumferential surface having a second diameter that is greater than the first diameter. The first and second portions each include a seal retention feature with a seal configured to create a leak-tight seal between the adaptable connector and a urostomy bag discharge conduit engaged thereon. The transition portion includes a tapered profile which guides the urostomy bag discharge conduit having a circumferential surface with a diameter different from the first portion diameter toward engagement with the second portion. A stop portion may be provided adjacent to the second portion opposite of the transition portion to limit the engagement of the urostomy bag discharge conduit with the barrel body.

In an embodiment, a drain assembly for attachment to a urostomy bag discharge conduit includes a connector having a barrel body adjacent to a first end, a flexible conduit extending from the connector opposite of the barrel body, and a discharge valve attached to the flexible conduit at a distal end of the flexible conduit. The barrel body further includes a first portion adjacent to the first end, a second portion, and a transition portion disposed between the first and second portions. The first portion has a circumferential surface having a first diameter. The second portion has a circumferential surface having a second diameter that is greater than the first diameter. The first and second portions each include a seal retention feature with a seal configured to create a leak-tight seal between the adaptable connector and a urostomy bag discharge conduit engaged thereon. A stop portion may be provided adjacent to the second portion opposite of the transition portion to limit the engagement of the urostomy bag discharge conduit with the barrel body and prevent interference with the flexible conduit.

In an embodiment, an adaptable connector includes a barrel body with a first end, a first portion adjacent to the first end, a second portion, and a transition portion disposed between the first and second portions. The first portion has a circumferential surface having a first diameter. The second portion has a circumferential surface having a second diameter that is greater than the first diameter. The first and second portions each include a seal retention feature with a seal configured to create a leak-tight seal between the adaptable connector and a urostomy bag discharge conduit engaged thereon. The first diameter and the second diameter are selected to provide a secure and leak-free interface with common urostomy bag discharge conduit configurations, for example, to allow use of the BobTail™ drain on a variety of urostomy bags.

Other features and advantages of the present invention will be apparent from the following more detailed description of the preferred embodiment, taken in conjunction with the accompanying drawings which illustrate, by way of example, the principles of the invention.

BRIEF DESCRIPTION OF DRAWINGS

Wherever possible, the same reference numbers will be used throughout the drawings to represent the same parts.

DETAILED DESCRIPTION OF THE INVENTION

Disclosed herein is a device and system that affords an ostomy bag wearer, such as a person that has had a urostomy, both greater discreet drainage of the urine waste from an ostomy bag and greater control of the flow of the urine waste. For example, the ostomy bag arrangement according to the present disclosure affords the male wearer a sense of normalcy while using a urinal. In addition, the ostomy bag arrangement according to the present disclosure affords peace of mind to both male and female users of ostomy bags that an ostomy bag can be conveniently, accurately, and discreetly emptied either into a urinal, toilet or other suitable waste receptacle.

A new and useful improvement to the drain assembly affords an ostomy bag wearer the advantage of connecting various products to different urostomy bags with a single adaptable connector.

Figure 1:
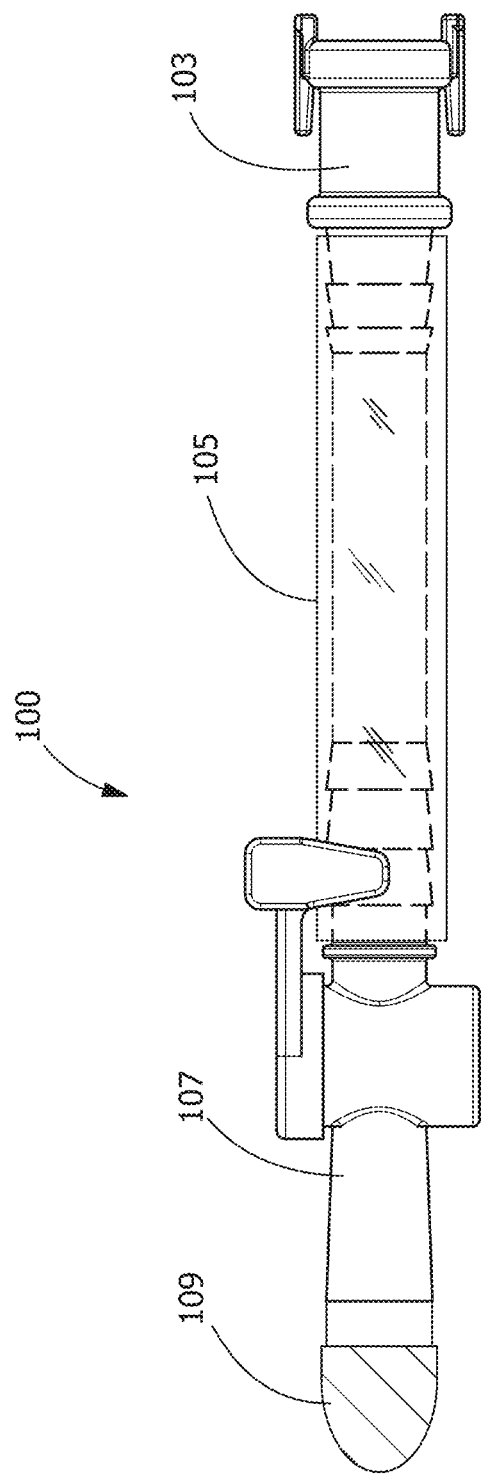
FIG. 1 schematically illustrates a drain assembly according to an embodiment of the present disclosure.
Figure 2:
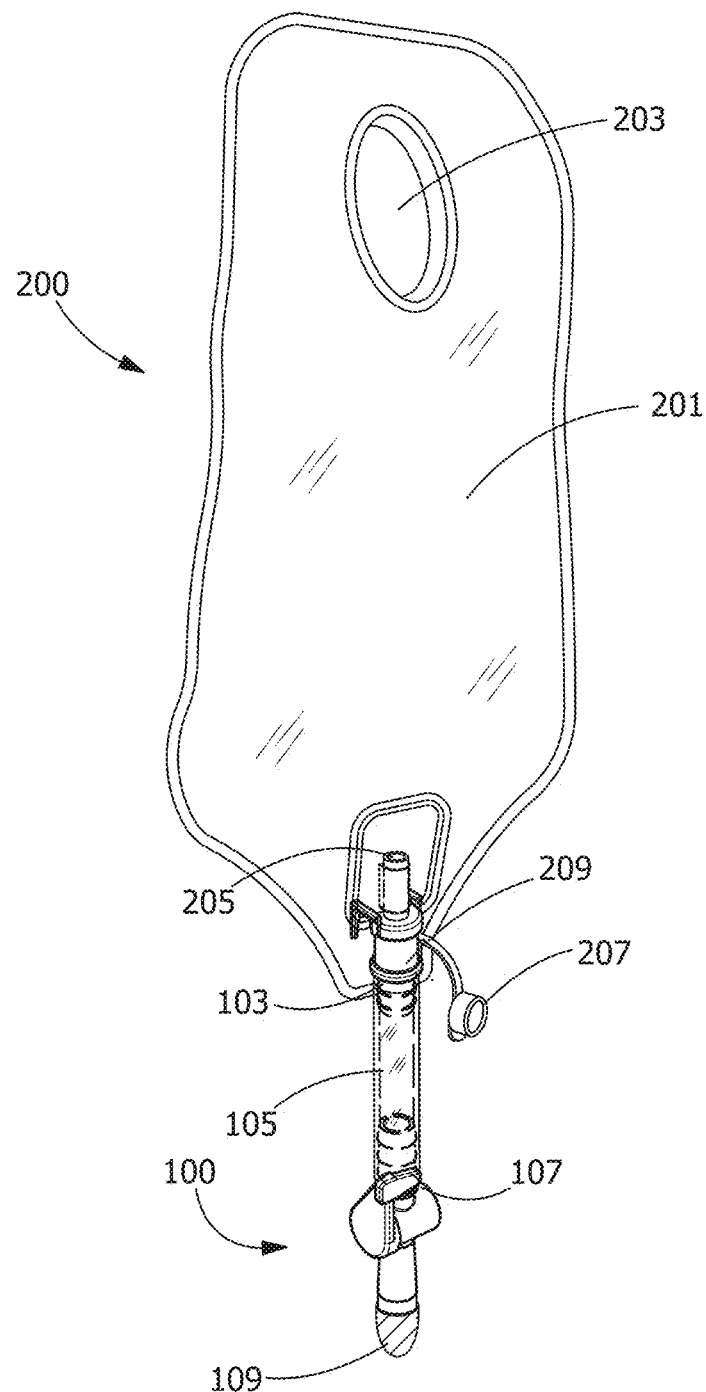
FIG. 2 schematically illustrates an urostomy bag assembly utilizing a drain assembly according to an embodiment of the present disclosure.
Figure 3:
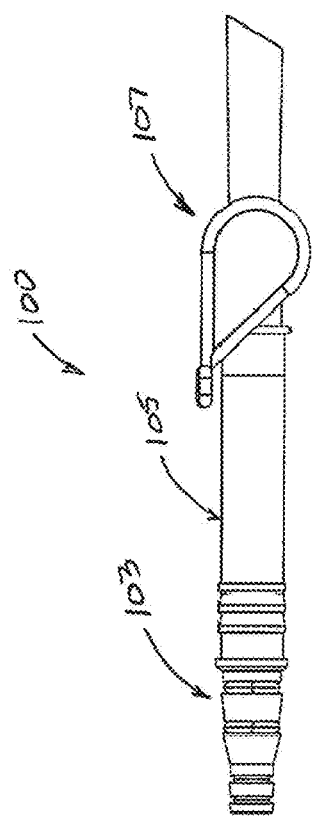
FIG. 3 illustrates an alternate embodiment of a drain assembly including an adaptable connector of the present disclosure.

FIGS. 1 and 2 show a drain assembly 100 (see FIG. 1) for use with an ostomy bag 201 and an ostomy bag arrangement 200 (see FIG. 2) according to an embodiment of the present disclosure. Drain assembly 100 includes a connector 103 configured to attach to the ostomy bag 201. Connector 103 detachably engages an ostomy bag 201. Connector 103 may include features, such as hooks, detents, threading, clips, fasteners, or any other connecting features that allow the connector to detachably engage the ostomy bag 201. In certain embodiments, the connector 103 may be a connector commercially available form the ostomy bag manufacturer for connection to other ostomy bag accessories, such as connections to night bags. A flexible conduit 105 attaches to and extends from the connector 103. The flexible conduit 105 may be connected to connector 103 as a unitary component or may be attached by a suitable attachment mechanism, such as a hose barb or tapered connector. There are various configurations of connectors 103. One type of connector 103 connects by snapping onto a port found at the distal end of the drainage valve located at the bottom of an ostomy bag 201 or pouch. Other connectors 103 connect by pushing in the male end of a tapered cone into the drainage tube once the plug is removed, best illustrated in FIG. 3. This type is used with bags which have no valve but use a tube with a plug. The drainage plug is pulled out and the cone is inserted. In one embodiment, connectors 103 have a configuration that may be used to connect a long tube, usually 4-6 feet, to drain opening of the ostomy bag 201 or pouch and at the distal end to connector to an overnight drainage collection system (not shown).

A discharge valve 107 is positioned at a distal end of the flexible conduit 105 from the connector 103. Like connector 103, the flexible conduit 105 may be attached to the discharge valve 107 by a suitable attachment mechanism, such as a hose barb or tapered connector, or the flexible conduit 105 and the discharge valve 107 may be a unitary component. The flexible conduit 105 is of a sufficient length and sufficient flexibility to permit an ostomy bag wearer 301 to position the discharge valve 107 into a discharge position outside of the ostomy bag wearer's 301 clothing for discharge of urine waste from the ostomy bag 201. Suitable lengths for the flexible conduit 105 include lengths or about 3 inches to about 8 inches. Alternately, the length of the drain assembly 100, including the flexible conduit 105, according to the present disclosure may be, for example, from 4 to 8 inches and may depend upon user preference. The length of the flexible conduit 105 has a length is sufficiently long to allow positioning of the discharge valve 107 into a location that permits drainage into a waste receptacle but is sufficiently short to avoid kinking or storage issues. In addition, if the total length of the drain assembly 100 is very short it is difficult and/or awkward to pull the drain assembly 100 through clothing to drain. If the drain assembly 100 is too short, the drain assembly 100 may slip into the underpants which may result in a requirement of the wearer to need to dig or reach for the drain assembly 100 inside their clothing. The length of the flexible conduit 105 serves to both allow convenient drainage of ostomy bag 201 and to permit the wearer to comfortably wear the ostomy bag arrangement 200. If the flexible conduit 105 is too long, the discharge valve 107 and the flexible conduit 105 may drop down the leg or lay against the genitals of the wearer.

Flexible conduit 105 may be fabricated from any suitable flexible material for contact with urine or other bodily fluids. For example, flexible conduit 105 may be a thermoplastic or fluoroplastic polymer, such as latex-free, vinyl tubing. Suitable materials for the flexible conduit 105 include, but are not limited to, polyethylene (PE), polyurethane (PU), polyvinylchloride (PVC), polytetrafluoroethylene (PTFE), fluorinated ethylene propylene (FEP) polyfluoroalkoxy alkane (PFA), polyvinylidene difluoride (PVDF), Polyether ether ketone (PEEK), silicone, nylon, Nalgene, thermoplastic elastomer (TPE) or any other suitable flexible tubing material. In addition to flexural modulus of the material of construction, the flexibility of the flexible conduit 105 is provided by the wall thickness. The diameter and the wall thickness of the flexible conduit 105 is a diameter suitable for draining of waster urine and flexible manipulation of the drain assembly 100. For example, in one embodiment, the diameter of the flexible conduit 105 may be from about 5 mm to about 15 mm, or from about 7 mm to about 13 mm, or from about 8 mm to about 10 mm or about 9 mm. Likewise, in one embodiment, the wall thickness may be from about 1.0 mm to about 2.0 mm or about 1.25 mm to about 1.75 mm or from about 1.4 mm to about 1.6 mm or about 1.5 mm. The flexibility of the material includes a flexural modulus that is sufficiently high or sufficiently stiff to maintain an open tube that allows flow of liquid, but also is sufficiently low or sufficiently flexible to permit movement and positioning of discharge valve 107. Further flexible conduit 105 is sufficiently flexible to avoid kinking and cutting off the flow of liquid. In addition, the flexible conduit 105 is sufficiently resilient to spring back to shape after being bent or compressed and/or sufficiently elastic to return to its shape quickly after being stretched or expanded. In addition, the flexible conduit 105 should have a hardness that is resistant to kinking at tight bends. Hardness of the flexible conduit 105 is measured as its durometer, and different scales, namely Shore A, Shore D, and Rockwell R, are commonly used for plastic and rubber materials. The lower the scale number, the softer and more flexible the material will be. For instance, a typical latex tubing hardness rating is Shore A35. Polyurethane tubing is not as soft and can measure between Shore A70 and A95. Harder materials like nylon and polyethylene are normally measured on the Shore D scale, and others (polypropylene, for example) use the Rockwell R scale. Flexibility may also be a function of hardness or durometer and wall thickness. In addition, the overall length of the flexible conduit 105 may also affect the flexibility. For example, a 6-inch-long flexible conduit 105 is more flexible than a 2½-inch flexible conduit. Lower durometer numbers are desired for the flexible conduit 105.

In one embodiment, the flexible conduit 105 may be formed from medical tubing commercially available from Thermo Fisher Scientific (Waltham, Massachusetts), Convatec (Reading, Berkshire, England, UK) or Saint Gobain Performance Plastics (La Défense, Courbevoie, France). A removable cap 109 may be optionally positioned over the discharge valve 107 to prevent undesired flow of urine from the discharge valve 107. Cap 109 may include a tether or similar retention feature to retain the cap 109 near the discharge valve 107 and prevent loss or dropping of the cap 109, for example in a urinal or toilet. In another embodiment, the flexible conduit 105 is a flexible corrugated tube to make it easier to bend from the bottom of the ostomy bag 201 to the zipper opening without bending or twisting the bag.

FIG. 2 shows an ostomy bag arrangement 200 according to an embodiment of the present disclosure. The ostomy bag arrangement 200 includes an ostomy bag 201 that is configured to receive waste urine from a person having a urostomy or other similar medical procedure that results in redirection of urine from the kidneys to a bag or reservoir outside of the body. "Ostomy bag", as utilized herein refers to bags or pouches utilized to collect urine. The terms ostomy "bag" and "pouch" are utilized interchangeably herein. For example, an ostomy bag wearer 301 may have had a urostomy. A urostomy is a surgery that creates a stoma in the patient's abdomen. Specifically, the stoma is attached to a place in the urinary tract to let urine leave the body. The majority of urostomies are placed on the right side and can be above the level of the umbilicus or below. At the stoma, the ostomy bag 201 may be attached or otherwise positioned on the wearer to collect urine for disposal. There are a number of configurations of ostomy bags 201, which are available from a number of different manufacturers. These ostomy bags 201 include an inlet opening 203 on a side of the ostomy bag 201 to receive urine from the stoma and a drain opening 205 at an end of the ostomy bag 201 that permits draining of the waste urine from the ostomy bag 201. As shown in FIG. 2, the ostomy bag 201 may include valve at the drain opening 205 to control the unintended flow of urine from the bag. While FIG. 2 shows this valve, the valve may be omitted and a cap 109, pin, pinched connection or other flow restraining features may be included. As shown in FIG. 2, a drain cap 207 in addition to the valve may be utilized to prevent the unintentional flow of urine.

The drain assembly 100 may attach to any ostomy bag 201, regardless of configuration or manufacturer, by configuring connector 103 to match the particular ostomy bag 201 discharge. The connector 103 detachably engages with a mating feature 209 of the ostomy bag 201. The mating feature 209 may include any suitable features, including barbs, tapers, threading, clips, protrusions, or other connecting features that detachable engage connector 103 and prevent leakage of liquid. These features may vary, for example, based upon manufacturer or ostomy bag configuration. For example, ostomy bags 201 are available from various manufacturers including Hollister (Libertyville, Illinois), Convatec (Reading, England, United Kingdom) and Coloplast (Humlebaek, Denmark). Connectors 103 that mate with the mating feature of 209 of these manufacturers may be of different diameters and configurations. The connectors 103, however, are integral to or connect to flexible conduit 105 of the drain assembly 100 according to an embodiment of the present disclosure. For example, connector 103 may include a hose barb or other connection suitable for connecting to the flexible conduit 105. The mating feature 209 and the connector 103 are detachable so that the drain assembly 100 may easily be removed from the ostomy bag 201 for either attachment to an ostomy bag accessory, such as a night receptacle, or so that the bag has a lower profile for the wearer for extended wear periods.

The connector according to present invention may connect the ostomy bag, via the extension connector/adapter, for example, to the BobTail™ drain which allows for easy and discreet emptying of a urostomy bag. The BobTail™ drain includes, for example, the valve assembly down and described in US Utility U.S. Pat. No. 11,701,249 and Design Pat. No. D978345S, each of which is incorporated by reference in their entirety.

Figure 5:
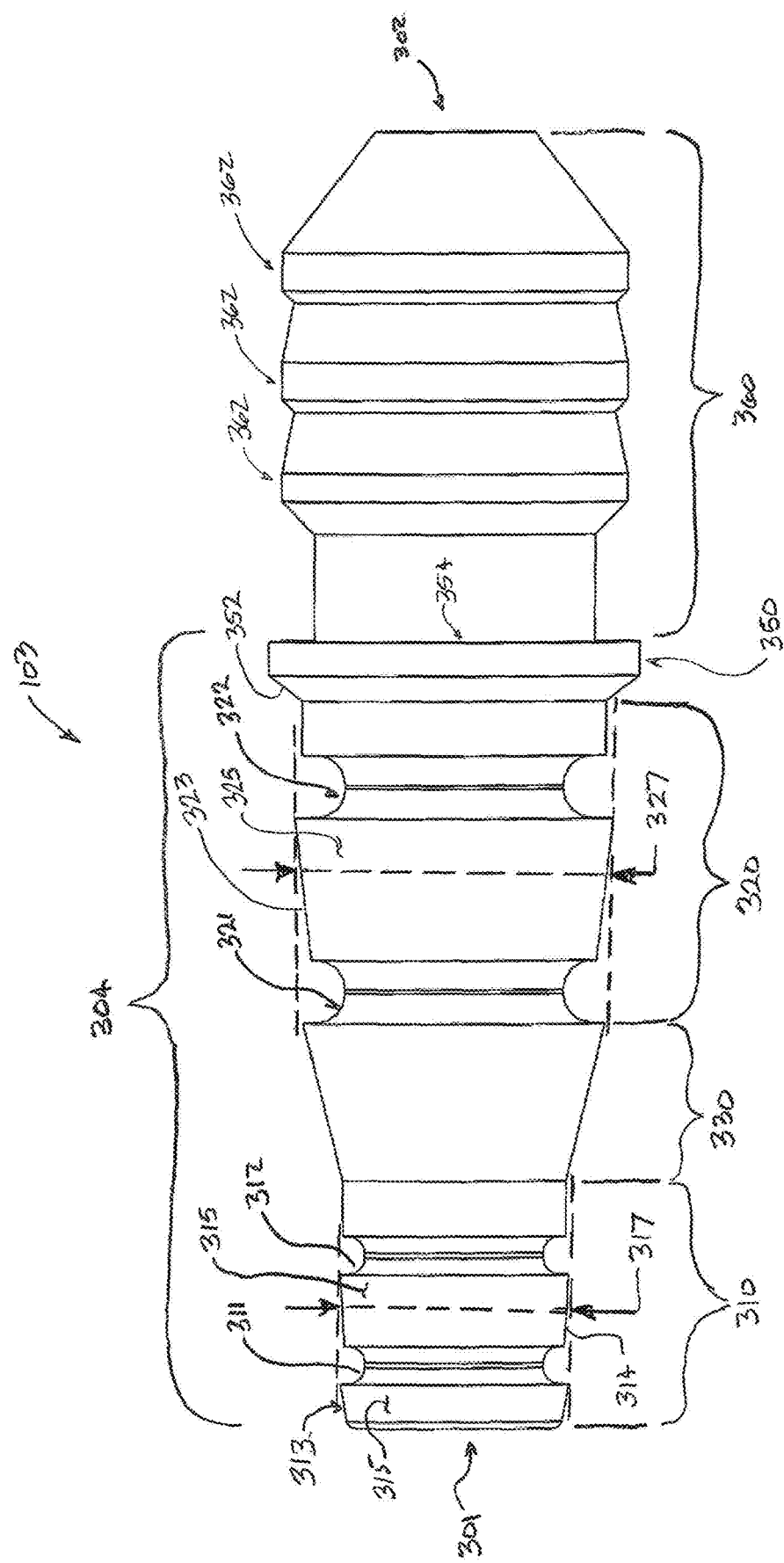
FIG. 5 illustrates an enlarged view of an embodiment of an adaptable connector of the present disclosure.
Figure 6:
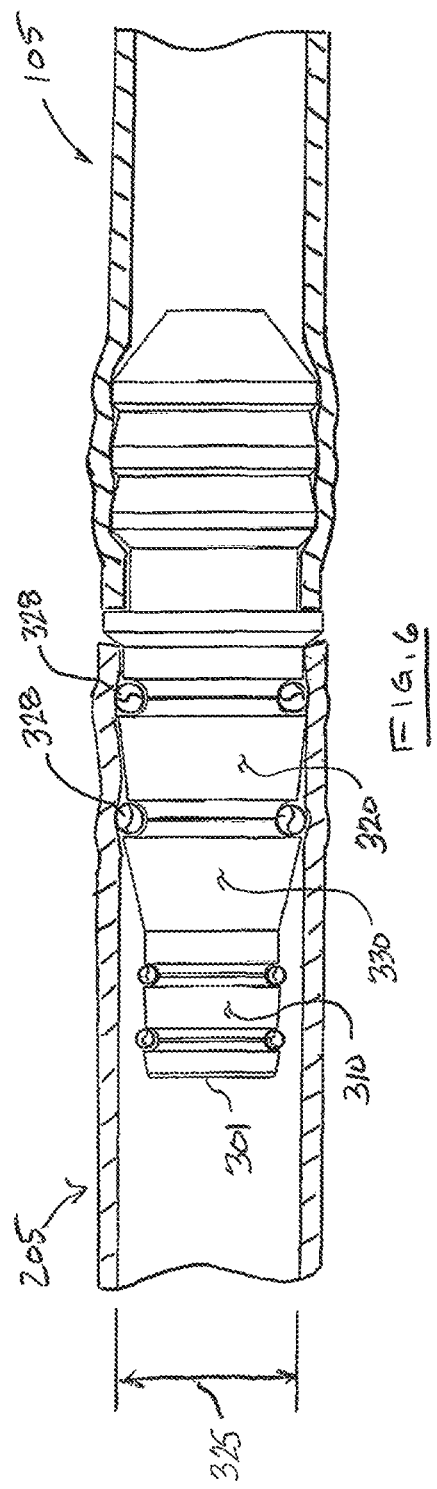
FIG. 6 illustrates an embodiment of an adaptable connector in use and
connected to a drain conduit of a first diameter.
Figure 7:
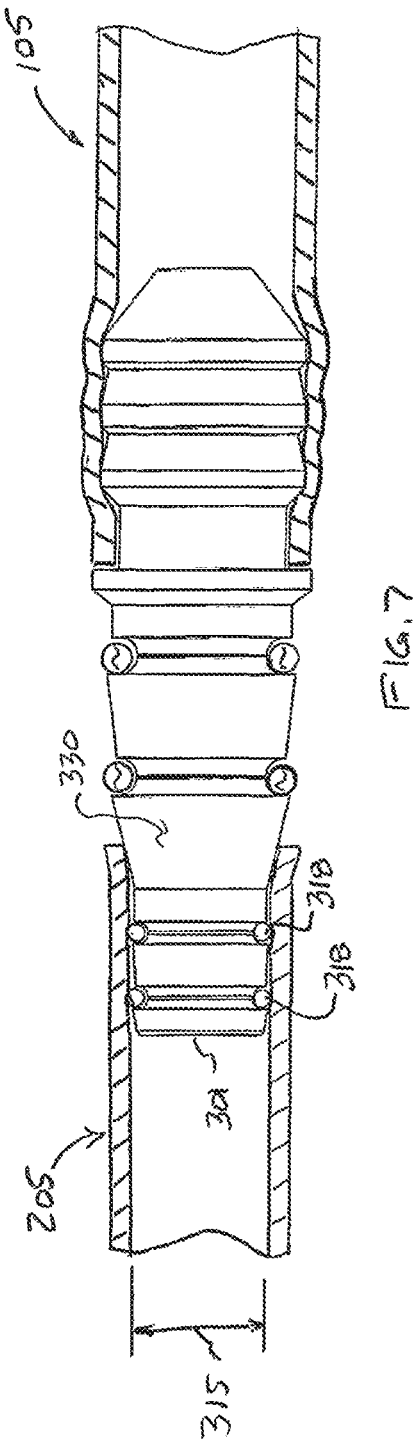
FIG. 7 illustrates an embodiment of an adaptable connector in use and connected to a drain conduit of a second, smaller diameter.

FIG. 5 shows adaptable connector 103 having a first end 301 and an oppositely disposed second end 302. In the embodiment shown in FIG. 5, the adaptable connector 103 is an elongate, generally cylindrical body structure with an exterior surface configured to interface with other fluid-conveying elements of the drain assembly and an interior bore or passageway allowing fluids to be conveyed through the connector 103. The adaptable connector 103 may be configured to connect adjacent conduits, one at each end to form a continuous flow path for fluids. The adjacent conduits may be of similar configuration, or they may be different. In the exemplar embodiment, the adaptable connector is configured to join the flexible conduit 105 of the drain assembly 100 with drain opening 205 of a urostomy bag.

The adaptable connector 103 may include a stop structure 350 intermediately disposed between the first end 301 and the second end 302. The stop structure defines the boundary between a conduit connected proximate to the first end 301 and a conduit connected proximate to the second end 302.

Figure 4:
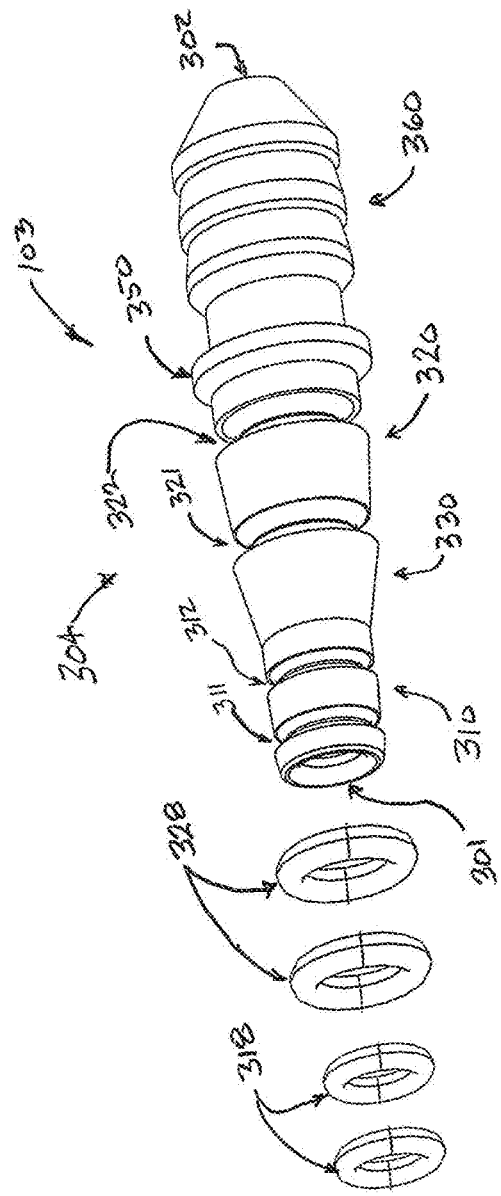
FIG. 4 illustrates an exploded view of an embodiment of an adaptable connector of the present disclosure.
Figure 8:
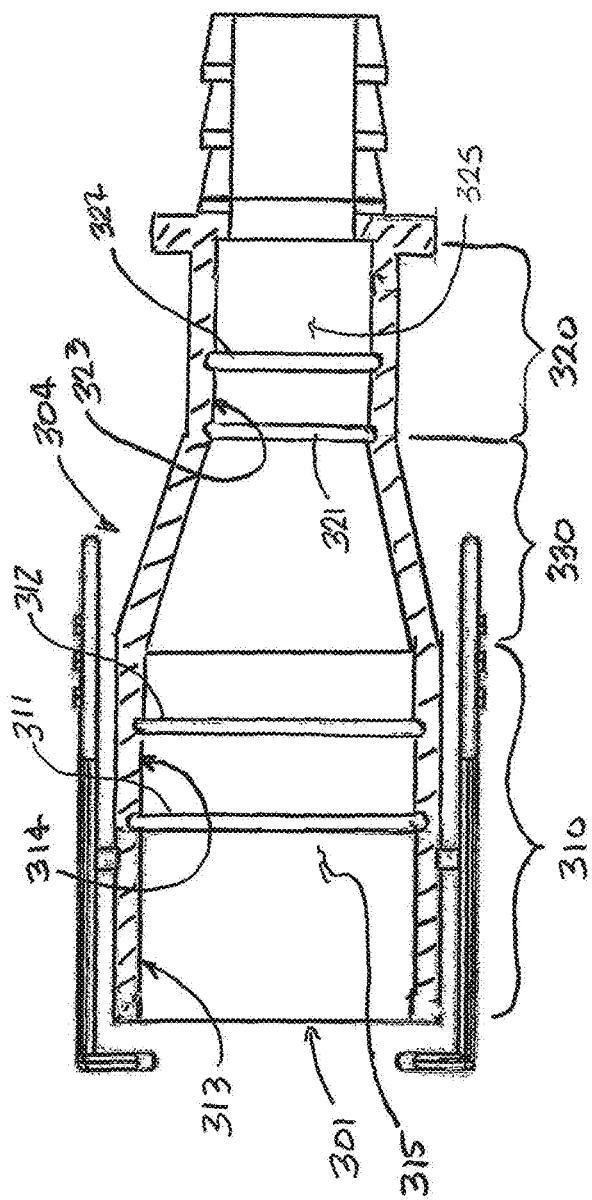
FIG. 8 illustrates an alternate embodiment of an adaptable connector configured to receive and seal to an external surface of a drain conduit.

Adaptable connector 103 includes a barrel body 304 having a first portion 310 disposed adjacent to the first end 301, a second portion 320, and a transition portion 330 disposed between the first and second portions. The first portion 310 has a circumferential surface 315 having a nominal first diameter 317 generally corresponding to a drain opening on a first urostomy bag. The second portion 320 has a circumferential surface 325 having nominal second diameter 327 corresponding to a drain opening on a second urostomy bag, the second drain opening being of different diameter than the first. In the exemplar embodiment of FIGS. 4 and 5, configured to seal with an interior surface of the drain conduit, second diameter 327 is greater than the first diameter 317. In an embodiment, the first diameter may be optimized for insertion and sealing with tubing having nominal inside diameters of ¼, 5/16, ⅜, 7/16, ½, ⅝, and ¾ inch. In an embodiment, the second diameter may be optimized for insertion and sealing with tubing having nominal inside diameters of 5/16, ⅜, 7/16, ½, ⅝, ¾, ⅞, and 1 inch. In an embodiment the first diameter may range between 0.25 inch and 1.00 inch and the second diameter may range between 0.25 and 1.00 inch. In an embodiment the first diameter may range between 0.25 inch and 0.075 inch and the second diameter may range between 0.30 and 1.00 inches. In an embodiment the first diameter may be 0.25 inches and the second diameter 0.40 inches. In the exemplar embodiment of FIGS. 4 and 5, second diameter 327 is greater than the first diameter 317. In an alternate embodiment of the adaptable connector shown in FIG. 8, the adaptable connector interfaces with an external surface of a drain conduit and thus the first diameter 317 is greater than the second diameter 327. The preferred diameters are selected to provide leak-free, sealed connections with the most common urostomy bag drain opening sizes. Other diameters may be specified as needed to adapt the adaptable connector for use with other ranges of urostomy bag drain openings.

The first and second portions 310, 320 each include one or more seal retention features 311, 312, 321, 322 extending circumferentially around the first and second portions. The seal retention features 311, 321 are configured to receive a seal member 318, 328. The seal retention features may be, for example, a groove, indentation or other similar feature and the seal members may be, for example, any suitable sealing structure, such as a gasket, O-ring, applied sealant or other sealing material or structure. The seal retention features are preferably contoured to match the contour of the seal member. In the illustrated exemplar, the seal retention feature is a groove having a radiused innermost portion matching the toroidal shape of the O-ring seal member. In an embodiment, the seal retention feature and the seal member may be integrally formed to produce an equivalent, projecting surface contour engageable with the discharge opening.

The first portion 310 adjacent to the first and 301 may include a chamfer or radius to guide the first end 301 into the drain opening or discharge conduit. The first portion 310 circumferential surface 315 may include tapered surfaces 313, 314 adjacent to the seal retention features 311, 312 angled to guide the over each seal member 318 to minimize damage during connection. The tapered surfaces 313, 314 may comprise individual tapered regions adjacent to each respective seal retention feature. The tapered surface regions may have similar surfaces forming taper angles and diameters, or the taper angles and diameters may be unique to each.

The transition portion 330 is generally tapered to transition from the first diameter to the second diameter. The transition portion 330 is generally tapered in configuration to guide larger drain openings into engagement with the second portion seal member(s) 328. The tapered portion 330 is also configured to guide the drain opening 205 across the seal member 328 positioned in seal retention feature 321 that it first interfaces with the drain opening as the barrel body is engaged.

The second portion 320 circumferential surface 325 may include a tapered surface portion 324 adjacent to the innermost seal retention feature 322 angled to guide the over the seal member 328 to minimize damage during connection.

The arrangement of the multiple nominal diameters, tapered surfaces, and seal members in the barrel body connection preferable for connection to the urostomy bag produce a watertight seal between the bag and the adaptable connector and enable the device to be inserted more easily than it is removed from the urostomy bag interface confirming that the device remains seated throughout regular use.

The separate seal members may be replaced further assuring optimal seal performance even as connection-disconnection cycles are increased.

The term "taper", "tapered" and grammatical variations thereof, as used herein, means a surface that is angled in relation to a longitudinal axis extending centrally between the first end and the second end of the adaptable connector. Tapered angles may be generally less than or equal to 20 degrees and are oriented so that diameters of tapered areas increase as displacement from the ends increases. Taper angles up to approximately 45 degrees may also be used in some transitions, particularly taper transitions adjacent to the connector ends.

The stop structure 350 is intermediately positioned between the opposing ends 301, 302 of the adaptable connector and limits the extent to which the adaptable connector may be received into a conduit. The stop structure 350 may be a flange-like structure extending radially beyond the nominal diameters of the adjacent connections. A barrel body 304, described above, may extend from both sides of the stop structure 350 toward the first and second ends, respectively. A conventional conduit connector structure 360 may be provided and extend from the stop structure 350 toward the second end 302. The conventional conduit connector structure 360 may include one or more barbs 362 known for connecting flexible tubing. The barbs entering the tubing are similar to many barbs used in many devices across the world.

The stop structure 350 may include stop faces 352, 354 to abut with the connected conduit. The stop faces 352, 354 may extend radially from a central axis of the adaptable connector. One or both stop faces 352, 354 may be angled to improve the seal with a connected conduit abutting the face.

Suitable material for the adaptable connector 103 targets a balance of rigidity and flexibility. Rigidity provides the user with confident and precise positioning of the device in the ostomy bag interface. The minor balance of flexibility provides a watertight seal, and some give allows the user to be confident that the device will stay seated due to the interference fit of the oversized flexible material.

Examples of components to which the inventive connector may be utilized, include, but are not limited to:
An ostomy or urostomy bag or pouch;
A nighttime drainage system;
A leg bag for larger amounts of fluid storage; and
Cleaning device that reverses the flow and pushes water through a disconnected bag.

While the exemplary embodiments illustrated in the figures and described herein are presently preferred, it should be understood that these embodiments are offered by way of example only. Accordingly, the present application is not limited to a particular embodiment, but extends to various modifications that nevertheless fall within the scope of the appended claims. The order or sequence of any processes or method steps may be varied or re-sequenced according to alternative embodiments.

It is important to note that the construction and arrangement of the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present application. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the exemplary embodiments without departing from the scope of the present application.

The invention claimed is:

1. A method for assembling an ostomy bag and drain assembly, the method comprising:
    providing the ostomy bag having a mating feature;
    providing a connector having a barrel body having a first end and a second end, the barrel body further comprising:
        a first portion disposed adjacent to the first end, the first portion having a first circumferential surface;
        a second portion having a second circumferential surface;
        a transition portion disposed between the first and second portions;
        a stop portion disposed adjacent to the second portion opposite of the transition portion; and
        a conduit connection structure extending from the stop portion toward the second end;
    directing the connector into engagement with the mating feature of the ostomy bag to attach and seal the connector to the mating feature;
    directing a flexible conduit onto the conduit connection structure to connect and seal the flexible conduit to the connector; and
    directing a distal end of the flexible conduit onto a discharge valve to attach and seal the flexible conduit to the discharge valve;
    wherein the barrel body engages the mating feature to establish a leak-free interface with the first portion or the second portion corresponding to a diameter of the mating feature.

2. The method of claim 1, further comprising directing a first seal onto the first portion into a seal retention member.

3. The method of claim 2, further comprising directing a second seal onto the second portion into a seal retention member.

4. The method of claim 3, wherein the first and second seal are O-rings.

5. A drain assembly for attachment to a mating feature of an ostomy bag comprising:
    a connector having a barrel body with a first end, the barrel body further comprising:
        a first portion disposed adjacent to the first end, the first portion having a first circumferential surface;
        a second portion having a second circumferential surface;
        a transition portion disposed between the first and second portions;
        a stop portion disposed adjacent to the second portion opposite of the transition portion; a stop portion disposed adjacent to the second portion opposite of the transition portion; and
        a conduit connection structure extending from the stop portion toward the second end;
    a flexible conduit attached and sealed onto the conduit connection structure; and
    a discharge valve attached to the flexible conduit at a distal end of the flexible conduit from the connector;
    wherein the barrel body engages the mating feature to establish a leak-free interface with the first portion or the second portion corresponding to a diameter of the mating feature.

6. The drain assembly of claim 5, wherein the first circumferential surface includes a first seal and a first seal retention feature, the first circumferential surface having a first diameter; the second circumferential surface includes a second seal and a second seal retention feature, the second circumferential surface having a second diameter.

7. The drain assembly of claim 6, wherein the diameter of the mating feature is an internal diameter of an inwardly facing circumferential surface.

8. The drain assembly of claim 7, wherein the first diameter is less than the second diameter.

9. The drain assembly of claim 6, wherein the diameter of the mating feature is an external diameter of an outwardly facing circumferential surface.

10. The drain assembly of claim 9, wherein the first diameter is greater than the second diameter.

11. The drain assembly of claim 6, wherein each of the first seal retention member and the second seal retention member are grooves.

12. The drain assembly of claim 11, wherein each or the first seal and the second seal are O-rings.

13. An adaptable connector for attaching a drain assembly to a mating feature of an ostomy bag, the adaptable connector comprising:
    a barrel body with a first end, the barrel body further comprising:
        a first portion disposed adjacent to the first end, the first portion having a first circumferential surface;
        a second portion having a second circumferential surface;
        a transition portion disposed between the first and second portions;
        a stop portion disposed adjacent to the second portion opposite of the transition portion; a stop portion disposed adjacent to the second portion opposite of the transition portion; and
        a conduit connection structure extending from the stop portion toward the second end;
    wherein the barrel body may be engaged by the mating feature to establish a sealed interface with the first portion or the second portion which corresponds to a diameter of the mating feature.

14. The adaptable connector of claim 13, wherein the first circumferential surface includes a first seal and a first seal retention feature, the first circumferential surface having a first diameter; the second circumferential surface includes a second seal and a second seal retention feature, the second circumferential surface having a second diameter.

15. The adaptable connector of claim 14, wherein the diameter of the mating feature is an internal diameter of an inwardly facing circumferential surface.

16. The adaptable connector of claim 14, wherein the first diameter is less than the second diameter.

17. The adaptable connector of claim 7, wherein the diameter of the mating feature is an external diameter of an outwardly facing circumferential surface.

18. The adaptable connector of claim 11, wherein the first diameter is greater than the second diameter.

19. The adaptable connector of claim 6, wherein each of the first seal retention member and the second seal retention member are grooves.

20. The adaptable connector of claim 11, wherein each or the first seal and the second seal are O-rings.

\* \* \* \* \*